(12) United States Patent
Goto et al.

(10) Patent No.: US 7,198,599 B2
(45) Date of Patent: Apr. 3, 2007

(54) ENDOSCOPE APPARATUS

(75) Inventors: Hiroaki Goto, Hachioji (JP); Tsuyoshi Nakagawa, Hachioji (JP); Yutaka Yanuma, Kunitachi (JP)

(73) Assignee: Olympus Corporation, Tokyo (JP)

( * ) Notice: Subject to any disclaimer, the term of this patent is extended or adjusted under 35 U.S.C. 154(b) by 305 days.

(21) Appl. No.: 10/448,539

(22) Filed: May 29, 2003

(65) Prior Publication Data

US 2004/0015050 A1    Jan. 22, 2004

(30) Foreign Application Priority Data

May 29, 2002  (JP)  ............................. 2002-155420
May 27, 2003  (JP)  ............................. 2003-149407

(51) Int. Cl.
*A61B 1/00*    (2006.01)

(52) U.S. Cl. ...................................... 600/154; 600/104
(58) Field of Classification Search ................ 600/104, 600/102, 153–159
See application file for complete search history.

(56) References Cited

U.S. PATENT DOCUMENTS 5,209,219 A * 5/1993 Hollobaugh ................ 600/154
5,921,971 A   7/1999 Agro et al.
6,299,576 B1 * 10/2001 Ouchi ........................ 600/106
6,315,774 B1 * 11/2001 Daniel et al. ................. 606/15
6,352,503 B1 *  3/2002 Matsui et al. ............... 600/104
6,395,003 B1    5/2002 Ouchi
6,827,683 B2 * 12/2004 Otawara ..................... 600/123

FOREIGN PATENT DOCUMENTS

| DE | 199 42 929 A1 | 3/2000 |
| JP | 8-71081 | 3/1996 |
| JP | 2000-157486 | 6/2000 |
| JP | 2001-340468 | 12/2001 |

* cited by examiner

*Primary Examiner*—Beverly M. Flanagan
(74) *Attorney, Agent, or Firm*—Scully, Scott, Murphy & Presser, P.C.

(57) ABSTRACT

A connecting device is designed releasably to connect a control section of an endoscope and a catheter control portion in a manner such that a channel opening portion in the control section of the endoscope and the catheter control portion are located close to each other.

12 Claims, 7 Drawing Sheets

ENDOSCOPE APPARATUS

CROSS-REFERENCE TO RELATED APPLICATIONS

This application is based upon and claims the benefit of priority from the prior Japanese Patent Application No. 2002-155420, filed May 29, 2002, the entire contents of which are incorporated herein by reference.

BACKGROUND OF THE INVENTION

1. Field of the Invention

The present invention relates to an endoscope apparatus, which is inserted into a patient's body cavity and used in high-frequency incision of an organic tissue, such as a duodenal papilla, or in confining an indwelling tube in a narrow segment, such as a biliary duct.

2. Description of the Related Art

In general, high-frequency incision or indwelling tubing in a patient's body cavity is carried out as a technique for treating the interior of the patient's body with use of an endoscope. After the endoscope is inserted in advance into the body cavity, in the high-frequency incision, a high-frequency knife is inserted into the body cavity through an instrument channel of the endoscope. Subsequently, high-frequency current is supplied to the knife, and an organic tissue in the body cavity is incised by means of the knife.

In the indwelling tubing in the body cavity, moreover, a guide wire is inserted into a narrow segment of the organic tissue through the instrument channel of the endoscope. Subsequently, an indwelling tube is inserted into the body cavity with use of the guide wire as a guide. Then, the tube is left in the narrow segment and used for drainage or the like.

For example, a high-frequency incision apparatus for endoscope is described in Jpn. Pat. Appln. KOKAI Publication No. 8-71081 (Patent Document 1). In this apparatus, the outlet of a lumen of a duodenal papilla, for example, is incised with high-frequency current.

In this apparatus, an electrically conductive wire is passed through an elongate flexible sheath. A high-frequency knife is connected electrically to the distal end portion of the wire. A control section is mounted on the proximal portion of the sheath. The control section is provided with an electric plug, a liquid feed connector, etc., which are connected electrically to the wire.

In using this apparatus, the high-frequency knife is inserted into a patient's body cavity through an instrument channel of an endoscope that is previously set in the body cavity. The knife is caused to approach the outlet of the lumen of the duodenal papilla as a target region, high-frequency current is supplied to the knife, and the lumen outlet is incised.

A biliary duct catheter is described in U.S. Pat. No. 5,921,971 (Patent Document 2). This catheter is provided with a guide wire lumen. The proximal portion of the catheter is formed having a liquid feed connector and a connector through which an elongate guide wire is passed. The catheter is inserted into a patient's body cavity through an instrument channel of an endoscope. Further, the guide wire is passed through the guide wire lumen of the catheter. Liquid feed or other operation can be carried out with the distal end portion of the guide wire kept close to a biliary duct.

The catheter can be also used in evacuating the biliary duct of pooled bile or the like. In doing this, an indwelling tube is guided to a narrow segment of the biliary duct through the channel of the endoscope. The indwelling tube is confined in the narrow segment, and bile in the biliary duct is discharged through the bore of the tube.

The endoscope is provided with a control section on the proximal end portion of an elongate insert section. The control section has an instrument inlet. The proximal end portion of an instrument channel is coupled to the instrument inlet. An insert section of an instrument, such as the high-frequency incision apparatus or the catheter apparatus described in Patent Document 1 or 2, is inserted into the instrument channel through the instrument inlet. The insert section of the instrument has flexibility such that it can bend tracing the curvature of the insert section of the endoscope. Thus, the insert section of the instrument inevitably hangs down unless those parts which project outward from the instrument inlet, e.g., the control section, connector portions on the proximal end portion of the insert section, etc., are held in a hand.

In carrying out incision by means of the high-frequency incision apparatus or indwelling tubing, therefore, a doctor usually holds the control section of the endoscope, while an assistant, such as a nurse, holds the guide wire, catheter, or some other instrument, in many cases. In these cases, the doctor gives instructions to the assistant while watching a monitor, and the assistant manipulates the instrument in accordance with the doctor's instructions.

BRIEF SUMMARY OF THE INVENTION

According to the present invention, there is provided an endoscope apparatus comprising: an endoscope; a catheter used in combination with the endoscope, the endoscope comprising an insert section which is inserted into a lumen, a control section coupled to the proximal end portion of the insert section, an instrument channel located in the insert section, and a channel opening portion which is located in the control section and communicates with the proximal portion of the instrument channel, the catheter having a catheter insert portion which is inserted into the instrument channel through the channel opening portion, the catheter insert portion having a guide wire lumen formed inside; a catheter control portion coupled to the proximal end portion of the catheter insert portion, the catheter control portion having at least one of a guide wire opening communicating with the guide wire lumen, a liquid feed opening and catheter control means; and a connecting device which releasably connects the control section of the endoscope and the catheter control portion in a manner such that the channel opening portion and the catheter control portion are located close to each other.

Preferably, according to the invention, the connecting device has an engaging hole formed near the channel opening portion and an engaging projection protruding from the catheter control portion and releasably in engagement with the engaging hole.

Preferably, according to the invention, the connecting device is located near the channel opening portion of the endoscope and has a catheter holding portion into which the catheter control portion is removably inserted, the catheter holding portion having retaining means which is elastically deformed so that the catheter control portion is releasably anchored when the catheter holding portion is penetrated by the catheter control portion.

Preferably, according to the invention, the retaining means has a cylinder provided with a slit in a part of the circumference thereof, and the cylinder is elastically deformed so that the catheter control portion is releasably fixed in a manner such that the width of the slit of the cylinder increases when the catheter control portion is inserted into the catheter holding portion.

Preferably, according to the invention, the catheter holding portion has an endoscope connecting portion removably mounted near the channel opening portion of the endoscope.

Preferably, according to the invention, the connecting device has an endoscope connecting portion provided on the catheter control portion and removably coupled to a coupling region near the channel opening portion of the endoscope, the endoscope connecting portion having two nip members opposed to and spaced from each other, an elastic member provided on that surface of at least one of the nip members which faces the other nip member, and retaining means which is releasably anchored to the coupling region of the endoscope in a manner such that the elastic member is elastically deformed when the two nip members are coupled to the coupling region so as to hold the coupling region.

Preferably, according to the invention, the connecting device comprises an endoscope connecting portion removably coupled to a coupling region near the channel opening portion of the endoscope and a catheter holding portion into which the catheter control portion is removably inserted.

Preferably, according to the invention, the endoscope connecting portion has a forceps plug located near the channel opening portion of the endoscope and a coupling plate removably coupled so as to be inserted in the gap between the forceps plug and a mounting seat.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
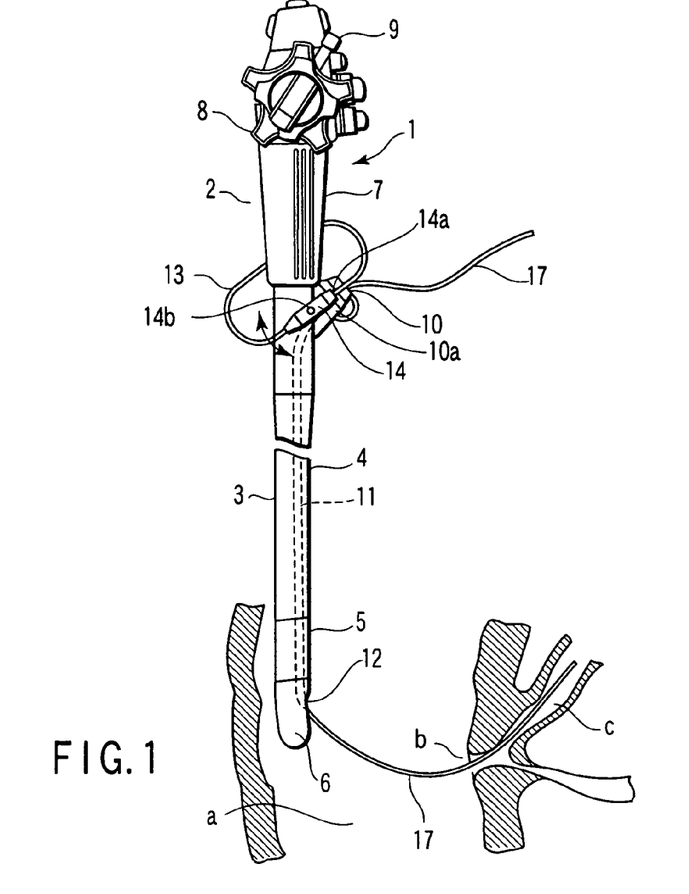
FIG. 1 is a side view showing the way an endoscope apparatus according to a first embodiment of the invention is used.
Figure 2A:
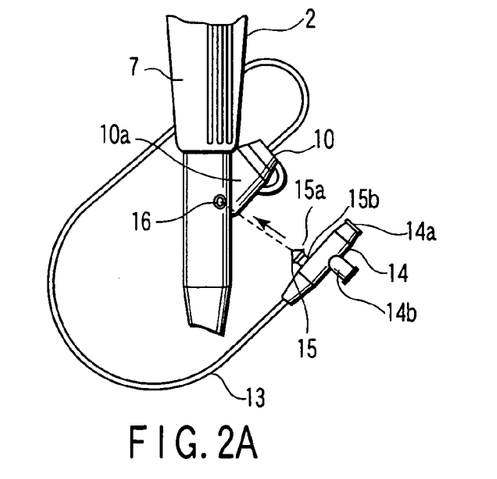
FIG. 2A is a perspective view showing a peripheral region around an instrument inlet of a control section according to the first embodiment.
Figure 2B:
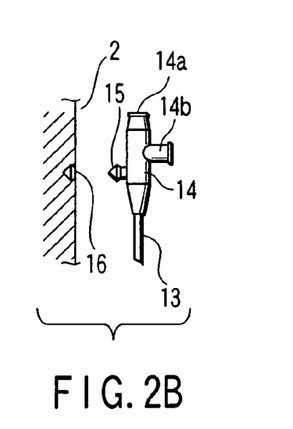
FIG. 2B is a longitudinal sectional view showing a mounting portion for a guide catheter cock.

Embodiments of the present invention will now be described with reference to the accompanying drawings. FIGS. 1, 2A and 2B show a first embodiment. FIG. 1 is a side view showing the way an endoscope apparatus is used. FIG. 2A is a perspective view showing a control section of an endoscope, and FIG. 2B is a longitudinal sectional view of the control section.

As shown in FIG. 1, the endoscope 1 comprises a control section 2 that is located outside a patient's body and an insert section 3 that is inserted into the body. The insert section 3 is composed of an elongate flexible tube portion 4, bending tube portion 5, and tip portion 6. The control section 2 is provided with a grip portion 7, control knob 8, control lever 9, and instrument inlet structure 10a. The knob 8 bends the tube portion 5. The lever 9 operates a forceps raiser (not shown). The inlet structure 10a is provided with a proximal-side channel opening portion 10 that communicates with the proximal end portion of an instrument channel 11 that is inserted in the insert section 3.

The tip portion 6 is formed having a distal-side channel port 12. The distal end portion of the instrument channel 11 communicates with the channel port 12.

A guide catheter 13, an instrument, can be inserted into the channel opening portion 10 of the instrument inlet structure 10a and guided into the instrument channel 11. Further, the catheter 13 in the channel 11 can be projected to the outside through the channel port 12 of the tip portion 6.

The guide catheter 13 is molded from a flexible synthetic resin material, e.g., fluorine- or nylon-based resin. It is formed having a guide wire lumen that extends throughout its length. A guide catheter cock 14 is provided on the proximal end of the catheter 13. The cock 14 has a guide wire opening 14a and a liquid feed connector 14b that communicates with the guide wire lumen.

An engaging projection 15 protrudes from a sidewall near the distal end of the guide catheter cock 14. The projection 15 has a tapered bulging portion 15a on its distal end portion and a constricted portion 15b on its proximal end portion. The projection 15 serves as an adapter or connecting device that releasably connects the control section 2 of the endoscope 1 and the catheter cock 14.

As shown in FIG. 2A, the control section 2 of the endoscope 1 is provided with an engaging hole 16 near the instrument inlet structure 10a. The engaging projection 15 of the guide catheter cock 14 can releasably engage the hole 16. The diameter of the bulging portion 15a of the projection 15 is larger than that of the engaging hole 16. The projection 15 is pushed into the hole 16 with the catheter cock 14 held in a hand, as indicated by the arrow of FIG. 2A. The bulging portion 15a of the engaging projection 15 is elastically deformed as it is inserted into the engaging hole 16, whereupon the projection 15 and the hole 16 elastically engage each other. Thus, the connecting device is formed so that the catheter cock 14 can be connected to the control section 2 at a stroke.

When the engaging projection 15 and the engaging hole 16 are in engagement with each other, the guide catheter cock 14 can rock around an engaging part between the engaging projection 15 and the engaging hole 16. Accordingly, the direction of the guide wire opening 14a of the catheter cock 14 can be aligned with the direction of the channel opening portion 10 of the instrument inlet structure 10a. Alternatively, a doctor may change the direction of the opening 14a at his/her choice.

Further, the engaging projection 15 and the engaging hole 16 can be easily disengaged from each other by separating the projection 15 from the hole 16 with the guide catheter cock 14 in a hand. Thus, the catheter cock 14 can be disconnected from the control section 2 at a stroke.

The following is a description of the operation of the first embodiment. FIG. 1 shows the way the endoscope apparatus of the present embodiment is used. In using the endoscope apparatus, the doctor first holds the grip portion 7 of the control section 2 of the endoscope 1 in one hand and the insert section 3 in the other as he/she inserts the insert section 3 into the patient's body cavity. The doctor observes an endoscopic image during the insertion and bends the bending tube portion 5 by manually operating the control knob 8 of the control section 2 if necessary. Thus, the insert section 3 of the endoscope 1 is introduced into the body cavity (duodenum a). The tip portion 6 is caused to approach a papilla b of the duodenum a.

Thereafter, a guide wire 17 is introduced into the body cavity (duodenum a) through the instrument channel 11 of the endoscope 1. In doing this, the doctor first holds the guide wire 17 in the other hand different from the hand in which the control section 2 of the endoscope 1 is held, and inserts the wire 17 into the channel 11 through the instrument inlet structure 10a. If the wire 17 is advanced by hand operation as this is done, its distal portion projects from the channel port 12 of the tip portion 6.

Subsequently, the doctor observes the distal portion of the guide wire 17 through a monitor as he/she operates the control lever 9 as required. This operation of the lever 9 causes the forceps raiser to rock, thereby controlling the direction of the distal portion of the wire 17. Then, the distal portion of the wire 17 is inserted into a biliary duct c through the papilla b. If the doctor then holds the proximal portion of the wire 17 and advances, retreats, or rotates the wire, he/she can insert the guide wire 17 into a target region while controlling the movement of its distal portion.

With the distal portion of the guide wire 17 thus inserted in the biliary duct c, the guide catheter 13 is inserted into the body cavity with the wire 17 used as a guide. In this operation, the guide catheter cock 14 is first connected to the control section 2. In doing this, the doctor holds the catheter cock 14 and pushes the engaging projection 15 into the engaging hole 16 of the control section 2. Thereupon, the projection 15 and the hole 16 are caused elastically to engage each other, and the catheter cock 14 is connected to the control section 2.

Thereafter, the guide wire 17 is fitted into the guide catheter 13 in a manner such that the proximal end of the wire 17 that projects outward from the instrument inlet structure 10a is inserted in the distal end of the catheter 13. The catheter 13 is advanced in this state. It moves with the wire 17 as a guide as it is passed through the instrument channel 11.

If the guide catheter 13 is advanced further, its distal portion projects from the channel port 12 of the tip portion 6 and is inserted into the biliary duct c through the papilla b. By holding the proximal portion of the guide wire 17 and advancing, retreating, or rotating the wire, also in this case, he/she inserts the distal portion of the guide catheter 13 into a target region while controlling the movement of its distal portion. When this is done, the guide catheter cock 14 is fixed to the control section 2 of the endoscope 1. Accordingly, the guide catheter 13 can be operated with the other hand different from the hand in which the control section 2 is held.

After the guide catheter 13 is inserted into the target region, moreover, a contrast medium, for example, is injected through the liquid feed connector 14b of the guide catheter cock 14. By doing this, the interior of the biliary duct c can be visualized. Thus, the position of the distal portion of the guide wire 17 can be confirmed under X-ray observation as the position of insertion of the catheter 13 is finely adjusted.

The configuration described above has the following effects. More specifically, according to the present embodiment, the guide catheter cock 14 can be attached to the control section 2 of the endoscope 1. Accordingly, the doctor can hold the control section 2 of the endoscope 1 in one hand as he/she operates the endoscope 1, and connect or disconnect the guide wire 17 and the guide catheter 13 and inject the contrast medium or the like with the other hand. Thus, the doctor can singly operate the endoscope 1 without being aided by an assistant, such as a nurse.

If the doctor is aided by the assistant when he/she operates the endoscope 1, he/she can hold the guide catheter cock 14 and separate it from the control section 2. If this is done, the engaging projection 15 gets out of the engaging hole 16, whereupon the catheter cock 14 can be disconnected from the control section 2.

In the embodiment described above, the guide catheter cock 14 and the control section 2 are provided with the engaging projection 15 and the engaging hole 16, respectively. In contrast with this, however, the catheter cock 14 and control section 2 may be provided with the hole 16 and the projection 15, respectively.

Figure 3A:
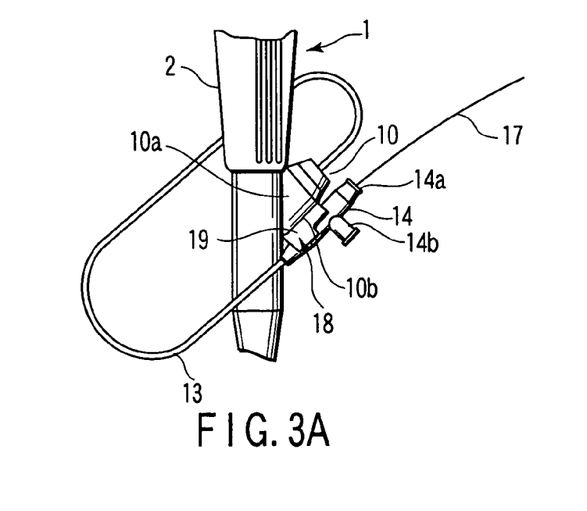
FIG. 3A is a side view of a control section of an endoscope according to a second embodiment of the invention.
Figure 3B:
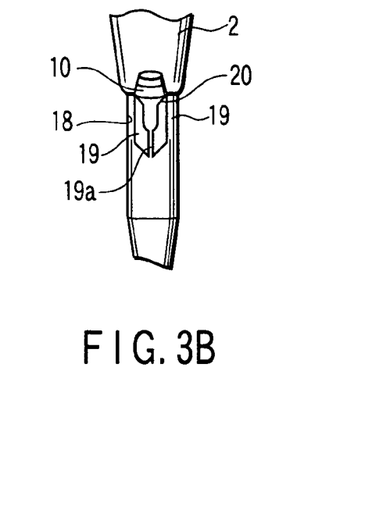
FIG. 3B is a front view of the control section.

FIGS. 3A and 3B show a second embodiment of the invention. FIG. 3A is a side view of a peripheral region around an instrument inlet of a control section of an endoscope, and FIG. 3B is a front view of the same region. Like numerals are used to designate the same components of the first and second embodiments, and a description of those components is omitted.

According to the present embodiment, an adapter 18 for use as a connecting device is provided on the outer peripheral surface of a cylinder portion 10b of an instrument inlet structure 10a on a control section 2 of an endoscope 1. In the adapter 18, a cylindrical portion 20 is formed by joining a pair of arcuate members 19 of a synthetic resin or metallic material so that their respective concave surfaces face each other. Formed between the arcuate members 19 is a slit 19a through which a guide catheter 13 can pass.

In attaching a guide catheter cock 14 to the adapter 18, therefore, it is held and inserted into the space between the arcuate members 19 from above the cylindrical portion 20 with the guide catheter 13 passed through a slit 19a between the arcuate members 19. By doing this, the catheter cock 14 can be attached to the adapter 18.

In removing the guide catheter cock 14 from the adapter 18, it is lifted up, and the guide catheter 13 is drawn out of the slit 19a.

The present embodiment shares functions and effects with the first embodiment, so that a description of the functions and effects is omitted.

Figure 4A:
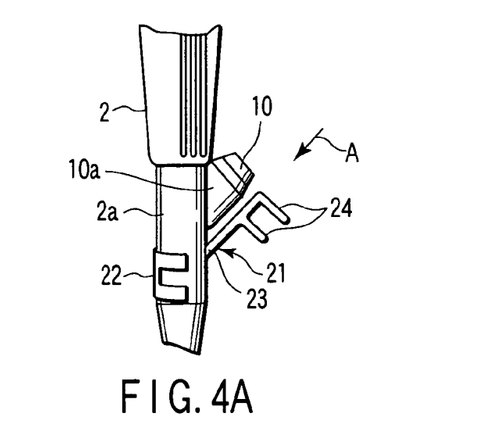
FIG. 4A is a side view of a control section of an endoscope according to a third embodiment of the invention.
Figure 4B:
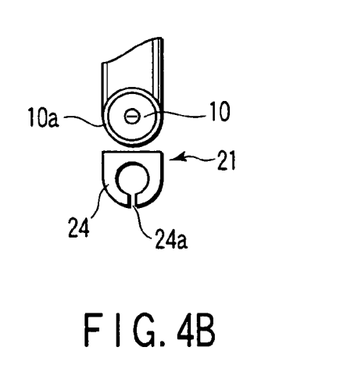
FIG. 4B is a view taken in the direction of the arrow of FIG. 4A.
Figure 5:
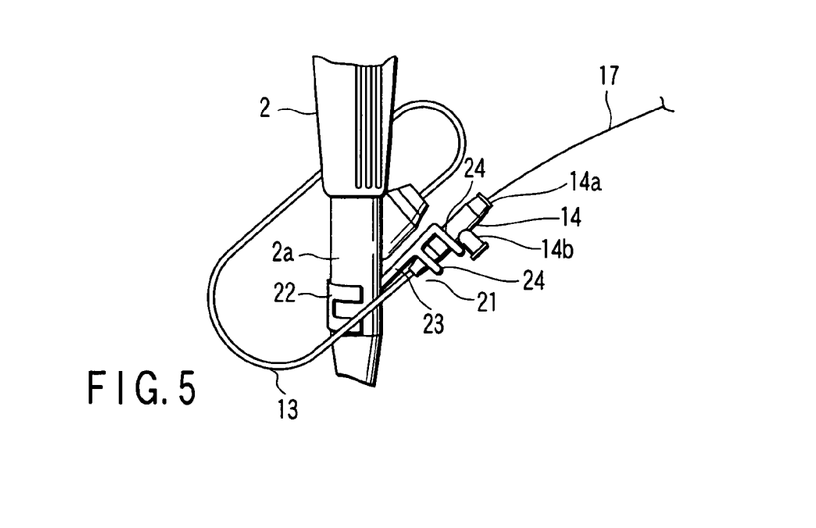
FIG. 5 is a side view of the control section of the endoscope fitted with a guide catheter cock according to the third embodiment.

FIGS. 4A, 4B and 5 show a third embodiment of the invention. FIG. 4A is a side view of a peripheral region around an instrument inlet structure of a control section of an endoscope, and FIG. 4B is a view taken in the direction of arrow A of FIG. 4A. FIG. 5 is a side view of the control section of the endoscope having a guide catheter cock thereon. Like numerals are used to designate the same components of the first and third embodiments, and a description of those components is omitted.

According to the present embodiment, a control section 2 of an endoscope 1 is provided with an adapter 21 for use as a connecting device. The adapter 21 is integrally formed of a synthetic resin material or the like. An arcuate mounting portion 22 is provided on the lower end portion of the adapter 21. It is elastically fitted on a cylinder portion 2a of the control section 2. The mounting portion 22 is provided with a support member 23 that projects diagonally upward so as to extend along an instrument inlet structure 10a in parallel relation. Cylindrical portions 24 are formed on the upper end portion of the support member 23 so that their respective concave surfaces face each other. The cylindrical portions 24, which are two in number, are spaced vertically, as shown in FIG. 4A. As shown in FIG. 4B, each cylindrical portion 24 is formed having a slit 24a through which a guide catheter 13 can pass.

In attaching a guide catheter cock 14 to the adapter 25, therefore, it is held and inserted into the adapter 21 from above the cylindrical portions 24 in a manner such that the guide catheter 13 is passed through the slits 24a with the catheter cock 14 held in a hand.

In removing the guide catheter cock 14 from the adapter 21, it is lifted up, and the guide catheter 13 is drawn out of the slits 24a.

The present embodiment shares functions and effects with the first embodiment, so that a description of the functions and effects is omitted.

Figure 6A:
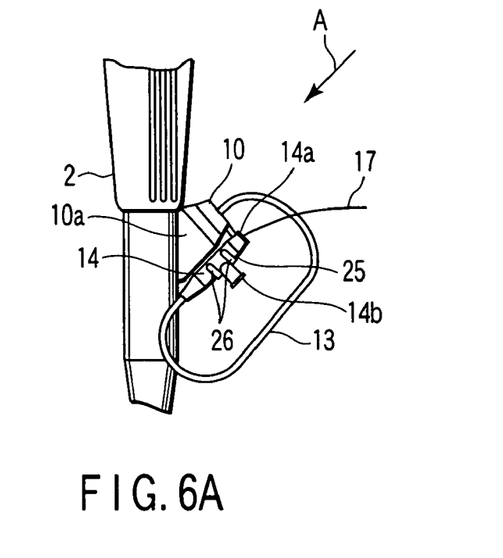
FIG. 6A is a side view of a control section of an endoscope fitted with a guide catheter cock according to a fourth embodiment of the invention.
Figure 6B:
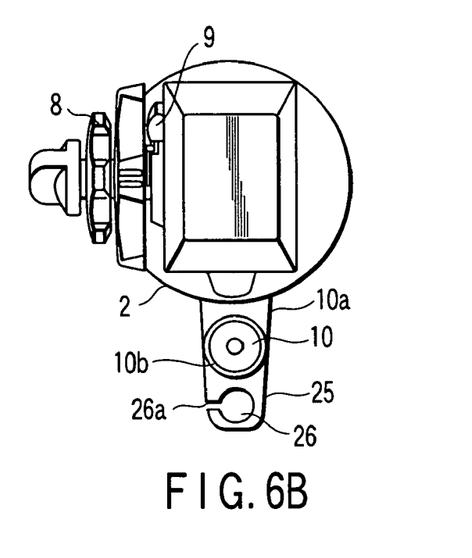
FIG. 6B is a view taken in the direction of arrow A of FIG. 6A.

FIGS. 6A and 6B show a fourth embodiment of the invention. FIG. 6A is a side view of a control section of an endoscope having a guide catheter cock thereon, and FIG. 6B is a view taken in the direction of arrow A of FIG. 6A. Like numerals are used to designate the same components of the first and fourth embodiments, and a description of those components is omitted.

According to the present embodiment, an instrument inlet structure 10a of a control section 2 is provided integrally with an adapter 25 for use as a connecting device. As shown in FIG. 6B, retaining rings 26 are formed on the adapter 25. They adjoin a cylinder portion 10b of the inlet structure 10a. The rings 26, which are two in number, are spaced vertically. The flank of each ring 26 is formed having a slit 26a through which a guide catheter 13 can pass.

In attaching a guide catheter cock 14 to the adapter 25, therefore, it is first held, and the guide catheter 13 is passed through the slit 26a. Subsequently, in this state, the catheter cock 14 is inserted into the retaining rings 26 from above. Thus, the catheter cock 14 can be attached to the adapter 25.

In removing the guide catheter cock 14 from the adapter 25, it is lifted up, and the guide catheter 13 is drawn out of the slits 26a.

Figure 7:
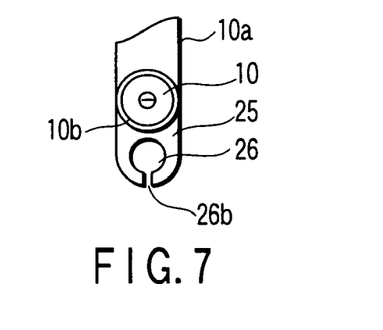
FIG. 7 is a plan view showing a modification of the fourth embodiment.

FIG. 7 shows a modification of the fourth embodiment. According to this modification, a slit 26b is formed in the front part of each retaining ring 26. The present embodiment shares functions and effects with the first embodiment, so that a description of the functions and effects is omitted.

Figure 8A:
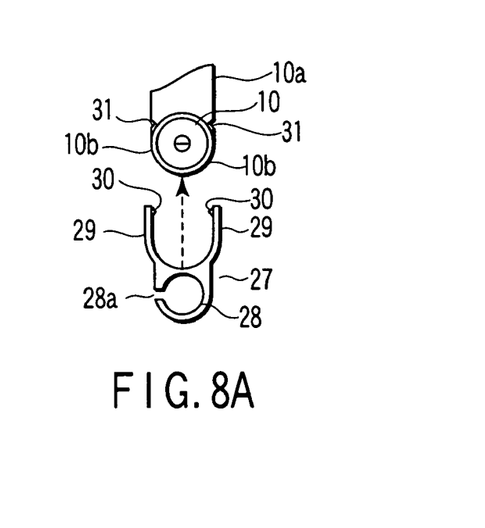
FIG. 8A is a plan view showing the way an adapter is attached to an instrument inlet according to a fifth embodiment of the invention.
Figure 8B:
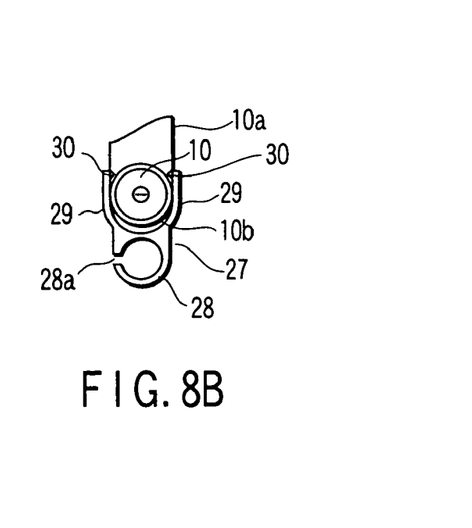
FIG. 8B is a plan view showing the instrument inlet fitted with the adapter.

FIGS. 8A and 8B show a fifth embodiment of the invention. FIG. 8A is a top view showing an instrument inlet structure 10a and an adapter 27 in a separate state. FIG. 8B is a top view showing the adapter 27 attached to the inlet structure 10a. Like numerals are used to designate the same components of the first and fifth embodiments, and a description of those components is omitted.

According to the present embodiment, the adapter 27 for use as a connecting device is removably attached to the instrument inlet structure 10a of a control section 2. The adapter 27 is integrally formed of a synthetic resin material. The adapter 27 is formed having a cylindrical portion 28 into which a guide catheter cock 14 is inserted. The flank of the cylindrical portion 28 is formed having a slit 28a through which a guide catheter 13 can pass.

Further, a pair of nip pieces 29 protrude from the back of the cylindrical portion 28. They can hold a cylinder portion 10b of the instrument inlet structure 10a between them. The respective distal end portions of the nip pieces 29 are provided individually with claw portions 30 that face each other. On the other hand, the cylinder portion 10b of the inlet structure 10a is provided with engaging recesses 31 that engage the claw portions 30, individually.

Thus, by pushing the nip portions 29 of the adapter 27 onto the cylinder portion 10b of the instrument inlet structure 10a, the claw portions 30 can be caused to engage the engaging recesses 31 so that the adapter 27 is fitted on the cylinder portion 10b.

In attaching the guide catheter cock 14 to the adapter 27, moreover, it is held and inserted into the cylindrical portion 28 from above with the guide catheter 13 passed through the slit 28a.

In removing the guide catheter cock 14 from the adapter 27, it is lifted up, and the guide catheter 13 is drawn out of the slit 28a.

The present embodiment shares functions and effects with the first embodiment, so that a description of the functions and effects is omitted.

Figures 9A, 9B:
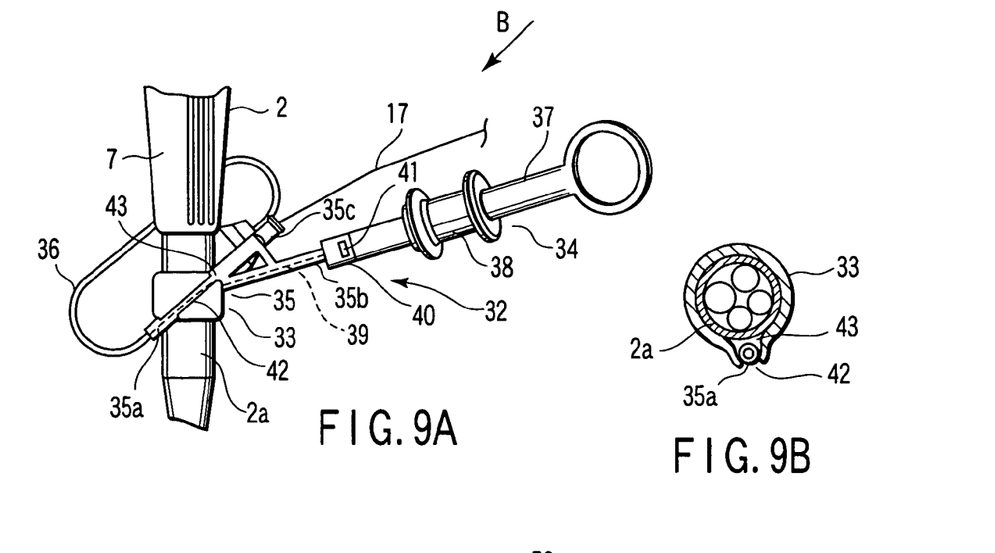
FIG. 9A is a side view of a control section of an endoscope according to a sixth embodiment of the invention.
FIG. 9B is a view taken in the direction of arrow B of FIG. 9A.

FIGS. 9A and 9B show a sixth embodiment of the invention. FIG. 9A is a side view of a control section of an endoscope, and FIG. 9B is a view taken in the direction of arrow B of FIG. 9A. Like numerals are used to designate the same components of the first and sixth embodiments, and a description of those components is omitted.

According to the present embodiment, an adapter 33 is used as a connecting device for attaching a high-frequency incision tool 32 to a control section 2 of an endoscope 1. The incision tool 32 will be described first. An incision tool body 34 is provided with a substantially Y-shaped coupling member 35. A common coupling portion 35a is provided on the distal end side of the coupling member 35. A pair of branch coupling portions 35b and 35c are arranged on the rear end side of the coupling member 35. The proximal end portion of a guide catheter 36 is coupled to the common coupling portion 35a.

Further, a control section body 37 is fixed to the one branch coupling portion 35b. A slider 38 is provided on the body 37 for movement in its longitudinal direction. The proximal end portion of an electrically conductive wire 39 is fixed to the slider 38 by means of a conductive control pipe 40 and a plug 41. A guide wire 17 is passed through the other branch coupling portion 35c.

The adapter 33 is a circular ring that is formed of a synthetic resin material. As shown in FIG. 9B, the adapter 33 is removably fitted on a cylinder portion 2a of the control section 2 of the endoscope 1. A slanting slit 42 is formed in a part of the circumference of the adapter 33. A slanting cylindrical portion 43 is formed so as to be continuous with the slit 42. The common coupling portion 35a of the high-frequency incision tool 32 can be inserted into the cylindrical portion 43.

In attaching the high-frequency incision tool 32 to the adapter 33, therefore, the control section body 37 held, the guide catheter 36 passed through the slit 42, and the common coupling portion 35a is inserted into the cylindrical portion 43 from above.

In removing the high-frequency incision tool 32 from the adapter 33, the control section body 37 is lifted up, and the guide catheter 36 is drawn out of the slit 42.

In incising the outlet of a lumen of a duodenal papilla by means of the high-frequency incision tool 32, according to the present embodiment, the doctor can hold the control section 2 of the endoscope 1 in one hand and insert the distal portion of the guide wire 17 into the lumen outlet with the other hand, as in the case of the first embodiment. Then, the doctor can make a high-frequency incision knife portion (not shown) to a target region to be subjected to high-frequency incision by inserting the guide catheter 36 of the incision tool 32 into the region using the wire 17 as a guide.

Figure 10A:
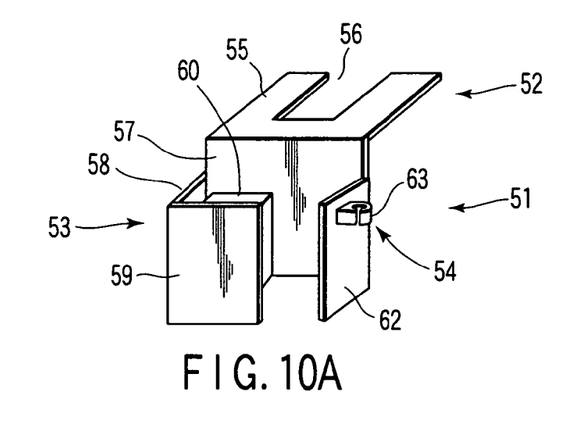
FIG. 10A is a perspective view of an adapter according to a seventh embodiment of the invention.
Figure 10B:
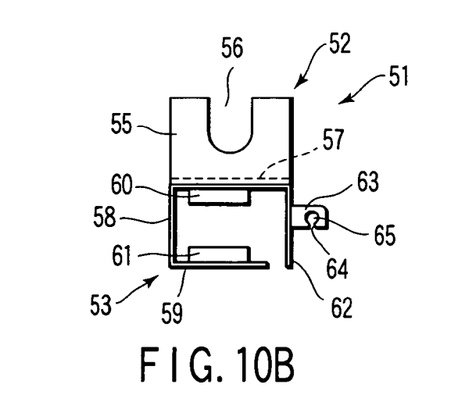
FIG. 10B is a plan view.

FIGS. 10A to 10C to FIGS. 13A and 13B show a seventh embodiment of the invention. Like numerals are used to designate the same components of the first and seventh embodiments, and a description of those components is omitted. According to the present embodiment, a control section 2 of an endoscope 1 is provided with an external removable adapter 51 shown in FIG. 10A, whereby a guide catheter 13, an instrument, is releasably anchored. The adapter 51 has an endoscope connecting portion 52, catheter connecting portion 53, and catheter end nip portion 54. As shown in FIG. 10B, the endoscope connecting portion 52 is formed of a substantially flat baseplate 55 that has an engaging recess 56. The adapter 51 is designed so that the engaging recess 56 of the baseplate 55 is attached to an instrument inlet structure 10a that is located on the control section 2 of the endoscope 1, as shown in FIG. 11B.

Figure 11A:
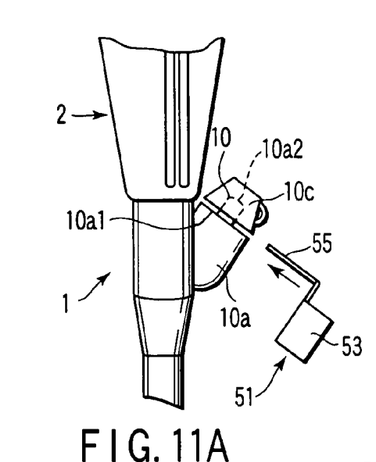
FIG. 11A is a side view showing the way the adapter is attached to a control section of an endoscope according to the seventh embodiment.
Figure 11B:
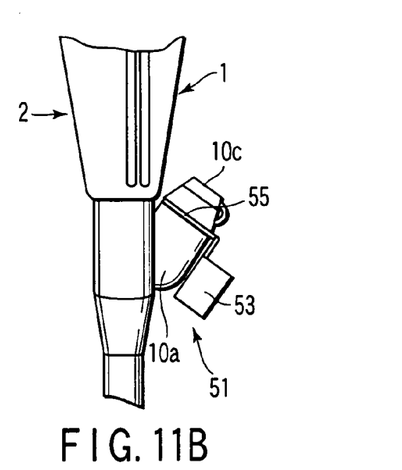
FIG. 11B is a side view showing the control section of the endoscope fitted with the adapter.
Figure 11C:
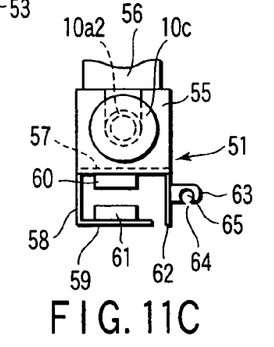
FIG. 11C is a plan view showing the adapter set in place.

At the distal end portion of the instrument inlet structure 10a, a tubular forceps plug mounting portion 10a2 protrudes from a forceps plug mounting seat 10a1, as is generally shown in FIG. 11A. A forceps plug 10c, which is formed of an elastic rubber member, is inserted and fitted into the plug mounting portion 10a2. Further, the adapter 51 is releasably fixed in a manner such that the baseplate 55 is inserted in the gap between the plug mounting seat 10a1 of the inlet structure 10a and the plug 10c and that the plug mounting portion 10a2 is inserted in the engaging recess 56 of the baseplate 55.

As shown in FIG. 10A, moreover, the catheter connecting portion 53 is provided with a flat first support plate 57 and a substantially L-shaped bent member 58. The support plate 57 is bent substantially at right angles to the baseplate 55. One end of the bent member 58 is coupled to the support plate 57. The bent member 58 is provided with a second support plate 59 that is opposed to the first support plate 57. The support plates 57 and 59 are spaced in parallel relation.

Figure 12A:
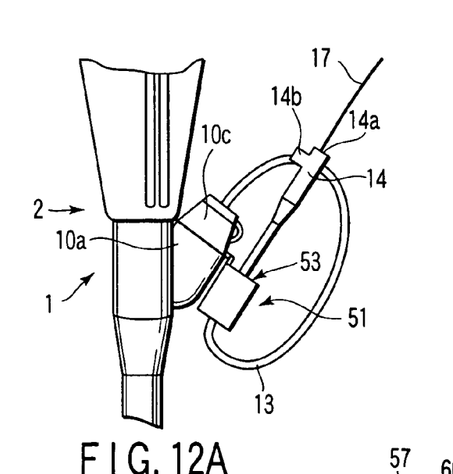
FIG. 12A is a side view of a principal part for illustrating the way of attaching a guide catheter cock to the operating adapter of the control section of the endoscope of the seventh embodiment.
Figure 12B:
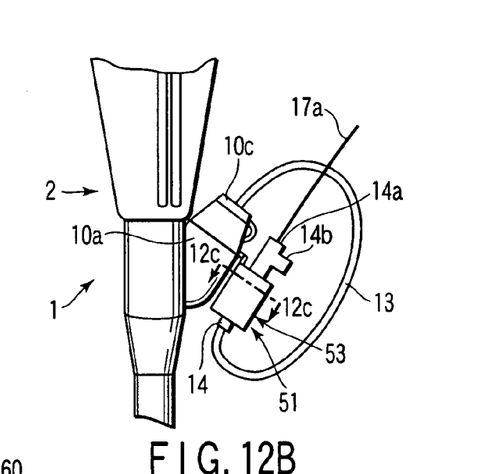
FIG. 12B is a side view of a principal part showing the guide catheter cock set in place.
Figure 12C:
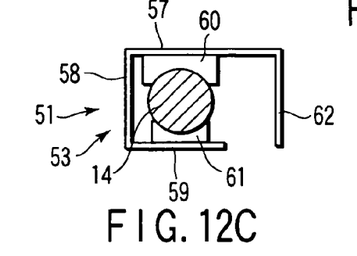
FIG. 12C is a sectional view taken along line 12C—12C of FIG. 12B.

As shown in FIG. 10B, furthermore, block-shaped elastic members 60 and 61 are attached to the respective inner surfaces of the first and second support plates 57 and 59. The elastic members 60 and 61 are opposed to and spaced from each other in parallel relation. As shown in FIG. 12C, a guide catheter cock 14 of the guide catheter 13 is releasably fixed to the catheter connecting portion 53 in a manner such that it is inserted and held in the gap between the elastic members 60 and 61. In general, the outside diameter of the catheter cock 14 is 7 mm or thereabout. Preferably, therefore, the distance between the first and second support plates 57 and 59 is adjusted to about 10 mm, and the distance between the two elastic members 60 and 61 to about 5 mm, for example.

Figure 10C:
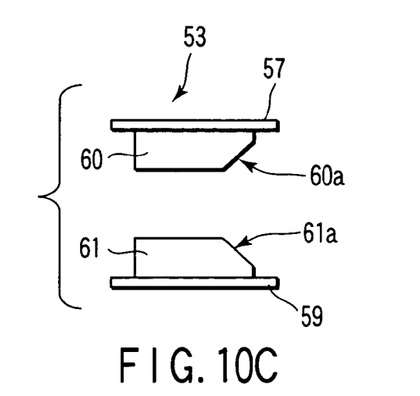
FIG. 10C is a plan view showing taper surfaces of elastic members.

As shown in FIG. 10C, moreover, slopes 60a and 61a are formed on one-side portions of the two elastic members 60 and 61, respectively. Thus, the space between the elastic members 60 and 61 gradually widens toward the distal end side.

Figure 13A:
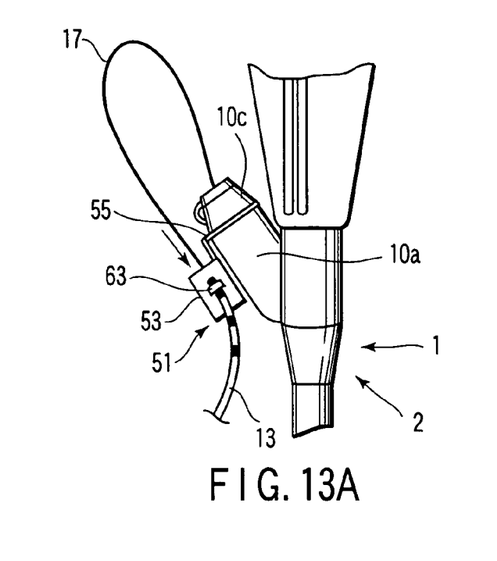
FIG. 13A is a side view of a principal part showing the distal end portion of a catheter held by means of an operating catheter holding portion of the adapter of the control section of the endoscope of the seventh embodiment.

As shown in FIG. 10A, the catheter end nip portion 54 is provided with a flat baseplate 62 that is coupled to that side of the first support plate 57 of the adapter 51 opposite from the bent member 58. As shown in FIG. 10B, a substantially cylindrical nip member 63 of an elastic material is attached to the outer surface of the baseplate 62. A narrow slit 64 is formed in a cylinder portion of the nip member 63. The inside diameter of a cylinder 65 of the nip member 63 is smaller than the outside diameter of the guide catheter 13. As the distal end portion of the catheter 13 is pressed into the cylinder 65 of the nip member 63, as shown in FIG. 13A, therefore, it is releasably fixed in a manner such that it is held by means of the nip member 63.

Silicone rubber, butyl rubber, or the like is used as the elastic material of the two elastic members 60 and 61 of the catheter connecting portion 53 and the nip member 63 of the catheter end nip portion 54, for example. Further, the first and second support plates 57 and 59 may be formed integrally with the elastic members 60 and 61, respectively.

The following is a description of the operation of the present embodiment arranged in this manner. In using the adapter 51 of the present embodiment, the endoscope connecting portion 52 of the adapter 51 is first attached to the instrument inlet structure 10a on the control section 2 of the endoscope 1. In doing this, the engaging recess 56 of the baseplate 55 of the connecting portion 52 is aligned with the plug mounting portion 10a2 of the inlet structure 10a, as shown in FIG. 11A. In this state, the baseplate 55 of the connecting portion 52 is inserted into the gap between the plug mounting seat 10a1 of the inlet structure 10a and the forceps plug 10c. The connecting portion 52 is releasably fixed to the inlet structure 10a in a manner such that the plug mounting portion 10a2 is inserted in the engaging recess 56 of the baseplate 55. Thereupon, the adapter 51 is fixed to the endoscope 1, as shown in FIG. 11B.

Figure 13B:
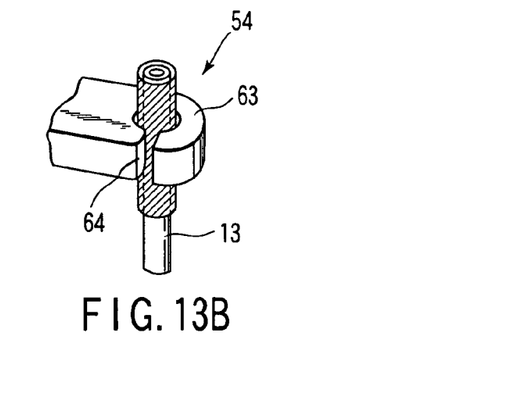
FIG. 13B is a perspective view of the principal part.

Subsequently, a distal end portion 13a of the guide catheter 13 is attached to the catheter end nip portion 54 of the adapter 51. In attaching the catheter 13, its distal end portion 13a is inserted into cylindrical nip member 63 of the catheter end nip portion 54 from below, as shown in FIG. 13B. Thereupon, the distal end portion 13a of the catheter 13 is held by means of the nip member 63 as it is fixed elastically. In this state, the proximal end of the guide wire 17 is inserted into the distal end of the catheter 13, as indicated by the arrow of FIG. 13A. Thereafter, the distal end portion 13a of the catheter 13 is disengaged from the nip member 63. Then, as in the cases of the foregoing embodiments, the catheter 13 is moved with used of the wire 17 as a guide as it is passed through the instrument channel 11, and is inserted into the patient's body through the channel 11.

Thereafter, the guide catheter cock 14 of the guide catheter 36 is attached to the catheter connecting portion 53 of the adapter 51. In attaching the catheter cock 14, it is held and inserted into the gap between the two elastic members 60 and 61 from above the catheter connecting portion 53, as indicated by the arrow of FIG. 12A, with the guide catheter 13 held between the elastic members 60 and 61, as shown in FIG. 12A. Thereupon, the catheter cock 14 is held and fixed between the two elastic members 60 and 61.

The configuration described above has the following effects. More specifically, the catheter connecting portion 53 of the adapter 51 according to the present embodiment is constructed so that the catheter cock 14 is held between the two block-shaped elastic members 60 and 61. Thus, any of catheter cocks 14 having various sizes and shapes such that they can be inserted into the gap between the two elastic members 60 and 61 can be releasably held by means of the catheter connecting portion 53 of the adapter 51.

Further, the adapter 51 of the present embodiment is provided with the catheter end nip portion 54, so that the distal end portion 13a of the catheter 13 can be releasably fixed by means of the nip portion 54. Since the proximal end of the guide wire 17 can be inserted into the distal end portion 13a of the catheter 13 in this state, insertion of the guide wire 17 is easy. Conventionally, a complicated operation is needed in separately holding the endoscope 1, the distal end of the catheter 13, and the proximal end of the guide wire 17. In consequence, according to the invention, this operation can be made easier when the doctor inserts the proximal end of the wire 17 into the distal end of the catheter 13.

Figure 14A:
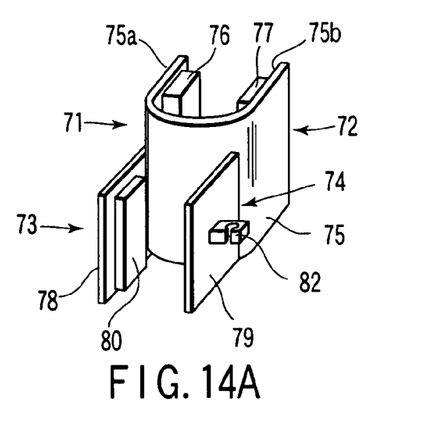
FIG. 14A is a perspective view of an adapter according to an eighth embodiment of the invention.
Figure 14B:
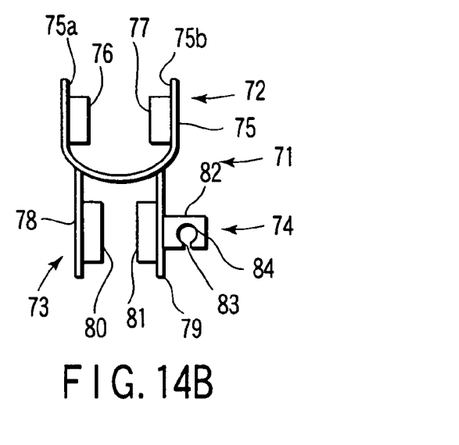
FIG. 14B is a plan view of the adapter.
Figure 14C:
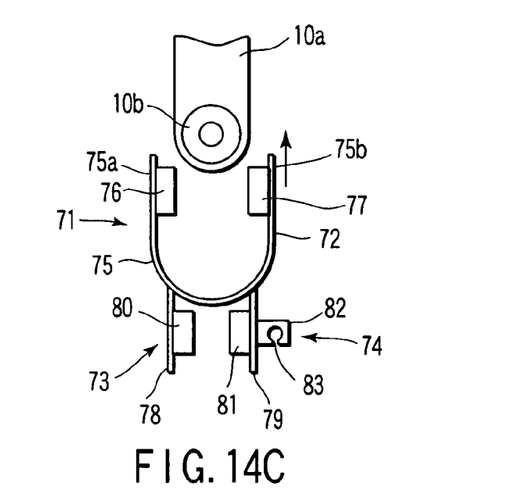
FIG. 14C is a plan view for illustrating operation for attaching the adapter to an instrument insert portion of and endoscope.
Figure 14D:
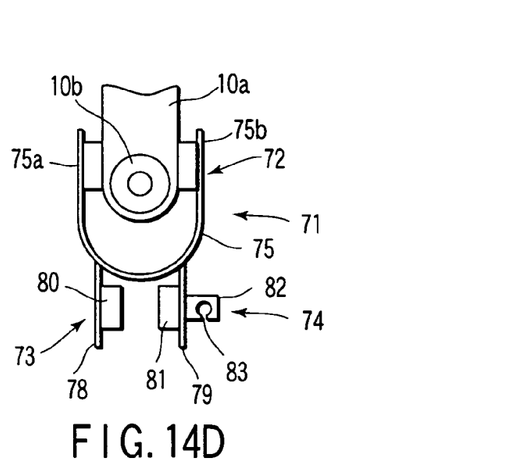
FIG. 14D is a plan view showing the instrument insert portion of the endoscope fitted with the adapter.
Figure 14E:
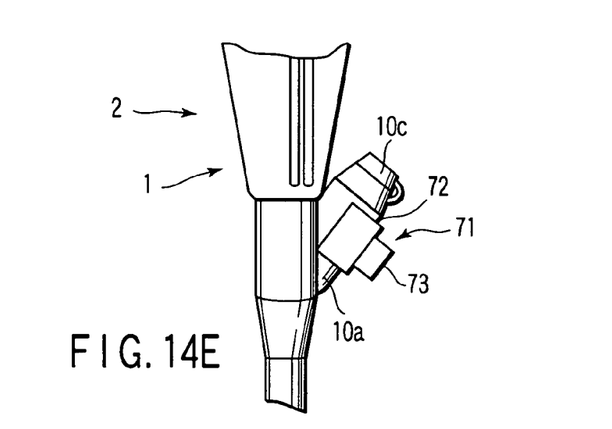
FIG. 14E is a side view showing the instrument insert portion of the endoscope fitted with the adapter.

FIGS. 14A to 14E show an eighth embodiment of the invention. Like numerals are used to designate the same components of the first and eighth embodiments, and a description of those components is omitted. An adapter 71 according to the present embodiment is constructed differently from the adapter 51 of the seventh embodiment (see FIGS. 10A to 10C to FIGS. 13A and 13B). The adapter 71 is provided with an endoscope connecting portion 72, catheter connecting portion 73, and catheter end nip portion 74. As shown in FIG. 14B, the endoscope connecting portion 72 is provided with a substantially U-shaped nip member 75. The nip member 75 is provided with a pair of retaining plates 75a and 75b that are spaced and opposed to each other in substantially parallel relation. Block-shaped elastic members 76 and 77 are attached to the respective inner surfaces of the retaining plates 75a and 75b. As shown in FIG. 14D, the adapter 71 is mounted in a manner such that the U-shaped nip member 75 of the endoscope connecting portion 72 is fitted on the instrument inlet structure 10a on the control section 2 of the endoscope 1.

As shown in FIG. 14A, moreover, the catheter connecting portion 73 is provided with a pair of support plates 78 and 79, which protrude from that side of the nip member 75 of the endoscope connecting portion 72 opposite from the retaining plates 75a and 75b.

As shown in FIG. 14B, moreover, block-shaped elastic members 80 and 81 are attached to the respective inner surfaces of the support plates 78 and 79. The elastic members 80 and 81 are opposed to and spaced from each other in parallel relation. A guide catheter cock 14 of a guide catheter 13 is releasably fixed to the catheter connecting portion 73 in a manner such that it is inserted and held in the gap between the elastic members 80 and 81. In general, the outside diameter of the catheter cock 14 is 7 mm or thereabout. Preferably, therefore, the distance between the two retaining plates 75a and 75b of the catheter connecting portion 73 is adjusted to about 10 mm, and the distance between the two elastic members 80 and 81 to about 5 mm, for example.

As shown in FIG. 14A, furthermore, the catheter end nip portion 74 has a substantially cylindrical nip member 82 of an elastic material that is attached to the outer surface of the one support plate 79 of the adapter 71, as shown in FIG. 14B. A narrow slit 83 is formed in a cylinder portion of the nip member 82. The inside diameter of a cylinder 84 of the nip member 82 is smaller than the outside diameter of the guide catheter 13. As the distal end portion of the catheter 13 is pressed into the cylinder 84 of the nip member 82, therefore, it is releasably fixed in a manner such that it is held by means of the nip member 82.

Silicone rubber, butyl rubber, or the like is used as the elastic material of the two elastic members 80 and 81 of the catheter connecting portion 73 and the nip member 83 of the catheter end nip portion 74, for example. Further, the nip member 75 may be formed integrally with the elastic members 76 and 77. Likewise, the support plates 78 and 79 may be formed integrally with the elastic members 80 and 81, respectively.

The following is a description of the operation of the present embodiment arranged in this manner. In using the adapter 71 of the present embodiment, the endoscope connecting portion 72 of the adapter 71 is first attached to the instrument inlet structure 10a on the control section 2 of the endoscope 1. In this attaching operation, the U-shaped nip member 75 moved in a direction such that it is fitted on the inlet structure 10a, as indicated by the arrow of FIG. 14C, and the adapter 71 is pushed in toward the inlet structure 10a. Thereupon, the inlet structure 10a is inserted into the gap between the respective elastic members 76 and 77 of the retaining plates 75a and 75b, as shown in FIG. 14D. Thus, the adapter 71 is attached to the instrument inlet structure 10a in a manner such that the inlet structure 10a is held between the elastic members 76 and 77. The present invention shares other functions with the seventh embodiment.

The configuration of the eighth embodiment described above can produce the same effects of the seventh embodiment.

Figure 15A:
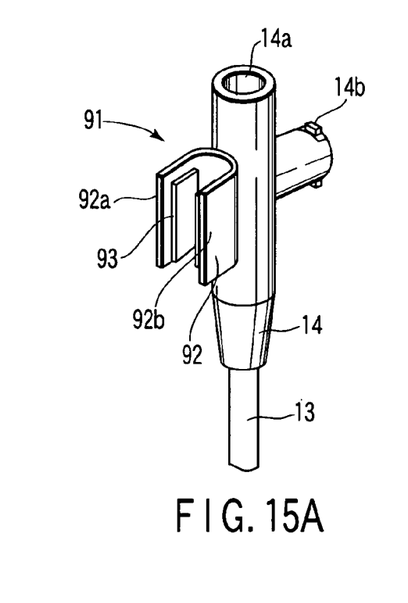
FIG. 15A is a perspective view showing an endoscope coupling portion of a guide catheter cock according to a ninth embodiment of the invention.
Figure 15B:
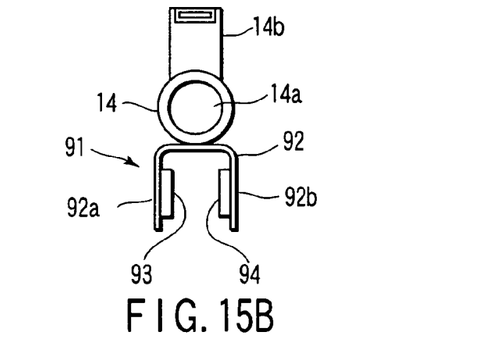
FIG. 15B is a plan view of the guide catheter cock.
Figure 15C:
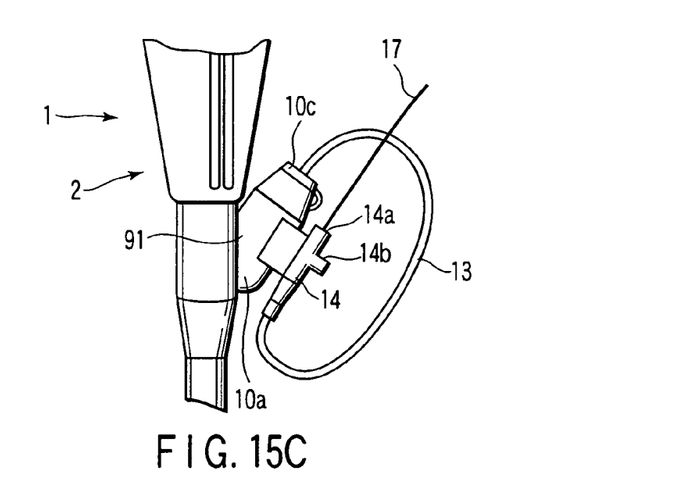
FIG. 15C is a side view showing the guide catheter cock coupled to the endoscope.

FIGS. 15A to 15C show a ninth embodiment of the invention. Like numerals are used to designate the same components of the first and ninth embodiments, and a description of those components is omitted. According to the present embodiment, a guide catheter cock 14 is provided with an endoscope connecting adapter 91. As shown in FIG. 15A, the adapter 91 is provided with a substantially U-shaped nip member 92. As shown in FIG. 15B, the nip member 92 is provided with a pair of retaining plates 92a and 92b that are spaced and opposed to each other in substantially parallel relation. Block-shaped elastic members 93 and 94 are attached to the respective inner surfaces of the retaining plates 92a and 92b. The endoscope connecting adapter 91 is mounted in a manner such that the U-shaped nip member 92 is fitted on an instrument inlet structure 10a that is located on a control section 2 of an endoscope 1, as shown in FIG. 15C.

Silicone rubber, butyl rubber, or the like is used as the elastic material of the two elastic members 93 and 94 of the endoscope connecting adapter 91. The nip member 92 may be formed integrally with the elastic members 93 and 94.

The following is a description of the operation of the present embodiment arranged in this manner. In using a guide catheter 13 of the present embodiment, the endoscope connecting adapter 91 of the guide catheter cock 14 is mounted in a manner such that the U-shaped nip member 92 is fitted on the instrument inlet structure 10a that is located on the control section 2 of the endoscope 1. The present invention shares other functions with the first embodiment.

The configuration of the eighth embodiment described above can produce the following effect. Since the guide catheter cock 14 of the present embodiment is provided with the endoscope connecting adapter 91, the adapter 91 of the catheter cock 14 can be releasably anchored to the instrument inlet structure 10a of the control section 2 of the endoscope 1, in using the guide catheter 13. In the present embodiment, as in the first embodiment, therefore, the doctor can simultaneously operate the endoscope 1 and the catheter 13. Thus, the operativity of the catheter 13 can be improved.

In any of the embodiments described herein, a guide catheter for feeding a liquid into a biliary duct or a guide catheter of a high-frequency incision tool for the outlet of a lumen of a duodenal papilla is introduced into a target region with use of a guide wire as a guide. It is to be understood, however, that the present invention is not limited to the embodiments described above, and that various changes and modifications may be effected therein without departing from the scope or spirit of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope apparatus comprising:
   an endoscope;
   a catheter used in combination with the endoscope, the endoscope comprising an insert section which is inserted into a lumen, a control section coupled to the proximal end portion of the insert section, an instrument channel located in the insert section, and a channel opening portion which is located in the control section and communicates with the proximal portion of the instrument channel, the catheter having a catheter insert portion which is inserted into the instrument channel through the channel opening portion, the catheter insert portion having a guide wire lumen formed inside;
   a catheter control portion coupled to the proximal end portion of the catheter insert portion, the catheter control portion having at least one of a guide wire opening portion communicating with the guide wire lumen, a liquid feed opening portion and a catheter control handle; and
   a connecting device which releasably connects the catheter control portion to the control section of the endoscope;
   wherein the connecting device has an engaging hole formed near the channel opening portion and an engaging projection protruding from the catheter control portion and releasably in engagement with the engaging hole.

2. An endoscope apparatus comprising:
   an endoscope;
   a catheter used in combination with the endoscope, the endoscope comprising an insert section which is inserted into a lumen, a control section coupled to the proximal end portion of the insert section, an instrument channel located in the insert section, and a channel opening portion which is located in the control section and communicates with the proximal portion of the instrument channel, the catheter having a catheter insert portion which is inserted into the instrument channel through the channel opening portion, the catheter insert portion having a guide wire lumen formed inside;
   a catheter control portion coupled to the proximal end portion of the catheter insert portion, the catheter control portion having at least one of a guide wire opening portion communicating with the guide wire lumen, a liquid feed opening portion and a catheter control handle; and
   a connecting device which releasably connects the catheter control portion to the control section of the endoscope;
   wherein the connecting device is located near the channel opening portion of the endoscope and has a catheter holding portion into which the catheter control portion is removably inserted, the catheter holding portion having a retaining member which is elastically deformed so that the catheter control portion is releasably anchored when the catheter holding portion is penetrated by the catheter control portion and wherein the retaining member has a cylinder provided with a slit in a part of the circumference thereof, and the cylinder is elastically deformed so that the catheter control portion is releasably fixed in a manner such that the width of the slit of the cylinder increases when the catheter control portion is inserted into the cylinder.

3. An endoscope apparatus comprising:
an endoscope;
a catheter used in combination with the endoscope, the endoscope comprising an insert section which is inserted into a lumen, a control section coupled to the proximal end portion of the insert section, an instrument channel located in the insert section, and a channel opening portion which is located in the control section and communicates with the proximal portion of the instrument channel, the catheter having a catheter insert portion which is inserted into the instrument channel through the channel opening portion, the catheter insert portion having a guide wire lumen formed inside;
a catheter control portion coupled to the proximal end portion of the catheter insert portion, the catheter control portion having at least one of a guide wire opening portion communicating with the guide wire lumen, a liquid feed opening portion and a catheter control handle; and
a connecting device which releasably connects the catheter control portion to the control section of the endoscope;
wherein the connecting device comprises an endoscope connecting portion removably coupled to a coupling region near the channel opening portion of the endoscope and a catheter holding a portion into which the catheter control portion is removably inserted and wherein the endoscope connecting portion has a forceps plug located near the channel opening portion of the endoscope and a coupling plate removably coupled so as to be inserted in the gap between the forceps plug and a mounting set.

4. The endoscope apparatus comprising:
an endoscope;
a catheter used in combination with the endoscope, the endoscope comprising an insert section which is inserted into a lumen, a control section coupled to the proximal end portion of the insert section, an instrument channel located in the insert section, and a channel opening portion which is located in the control section and communicates with the proximal portion of the instrument channel, the catheter having a catheter insert portion which is inserted into the instrument channel through the channel opening portion, the catheter insert portion having a guide wire lumen formed inside;
a catheter control portion coupled to the proximal end portion of the catheter insert portion, the catheter control portion having at least one of a guide wire opening portion communicating with the guide wire lumen, a liquid feed opening portion and a catheter control handle; and
a connecting device which releasably connects the catheter control portion to the control section of the endoscope;
wherein the catheter control portion is connected to the control section of the endoscope such that the catheter control portion is relatively movable in the arbitrary direction and the connecting device includes a moving mechanism for moving the catheter control portion with respect to the control section of the endoscope.

5. An endoscope apparatus comprising:
an endoscope comprising a distal end portion and a proximal end portion, the distal end portion including an insert section which is inserted into a lumen, and the proximal end portion including a control section for controlling the insert section, wherein an instrument channel communicating from the control section to the distal end portion of the insert section is formed inside the endoscope, and a channel opening portion communicating with the channel is located in the control section to insert an instrument into the instrument channel and;
a catheter comprising a distal end portion and a proximal end portion, the distal end portion including an insert section inserted from the channel opening portion of the endoscope to the instrument channel, and the proximal end portion including a control section for controlling the insert section, wherein a lumen communicating from the proximal end portion to the distal end portion is formed inside the insert section of the catheter, and an opening communicating with the lumen is located in the control section of the catheter; and
a connecting device which releasably connects the control section of the endoscope and the catheter control portion in a manner such that the channel opening portion and the catheter control portion are located close to each other.

6. The endoscope apparatus according to claim 5, wherein the connecting device connects the control section of the endoscope and the catheter control portion in a manner such that the channel opening portion and the opening of the catheter control portion substantially face the same direction.

7. The endoscope apparatus according to claim 5, wherein the connecting device arbitrarily adjusts the direction of the opening of the catheter control portion with respect to the channel opening portion when connecting the catheter control portion to the control section of the endoscope.

8. The endoscope apparatus according to claim 5, further comprising a treatment portion, located at the distal end portion of the catheter, for carrying out a predetermined treatment, and an instrument control handle, located at the proximal end portion, for controlling the treatment portion, wherein
the connecting device releasably connects the catheter control portion and the instrument control handle to the control section of the endoscope in a manner such that the channel opening portion, the opening of the catheter control portion, and the instrument control handle are located close to each other.

9. A connecting device comprising:
a connection section body;
a first connecting portion, located on the connection section body, for connecting the connection section body to an endoscope including:
an insert section which is inserted into a lumen;
a control section coupled to a proximal end portion of the insert section;
an instrument channel disposed inside the insert section; and
a channel opening portion communicating with the instrument channel, and
a second connecting portion, located on the connection section body, for connecting the connection section body to a catheter including:
an insert section inserted into the instrument channel from the channel opening portion of the endoscope;
a control section coupled to the proximal end portion of the insert section;
a lumen formed inside the insert section; and an opening located at the control section communicating with the lumen, wherein
the connection section body releasably connects the control section of the endoscope and the catheter control portion in a manner such that the channel opening portion and the catheter control portion are located close to each other.

10. The connecting device according to claim 9, wherein the connection section body connects the control section of the endoscope and the catheter control portion in a manner such that the channel opening portion and the opening of the catheter control portion substantially face the same direction.

11. An endoscope apparatus comprising:
an endoscope comprising a distal end portion and a proximal end portion, the distal end portion including an insert section which is inserted into a lumen of a living body, and the proximal end portion including a control section for controlling the insert section, wherein an instrument channel communicating from the control section to the distal end portion of the insert section is formed inside the endoscope, and a channel opening portion communicating with the channel is located in the control section to insert an instrument into the instrument channel;
an instrument comprising a distal end portion and a proximal end portion, the distal end portion including a treatment portion, inserted from the channel opening portion of the endoscope into the instrument channel, for carrying out a predetermined treatment in the lumen, and the proximal end portion including a control portion for controlling the treatment portion, wherein an instrument control handle for carrying out a treatment operation at the treatment portion according to an operation by an operator is provided in the control portion of the instrument; and
a connecting device which releasably connects the control section of the endoscope and the catheter control portion in a manner such that the channel opening portion and the instrument control handle of the instrument control portion are located close to each other.

12. The endoscope apparatus according to claim 11, wherein the connecting device arbitrarily adjusts the direction of the control handle of the instrument control portion with respect to the channel opening portion when connecting the instrument control portion to the control section of the endoscope.

* * * * *